United States Patent [19]
Eckstein et al.

[11] Patent Number: 5,480,434
[45] Date of Patent: Jan. 2, 1996

[54] METHOD AND DEVICE FOR CONNECTING BIOLOGICAL DUCT TO A PROSTHESIS

[75] Inventors: Eugene C. Eckstein; Norman L. Block, both of Miami, Fla.

[73] Assignee: The University of Miami, Miami, Fla.

[21] Appl. No.: 91,818

[22] Filed: Jul. 13, 1993

[51] Int. Cl.⁶ .................................................... A61F 2/04
[52] U.S. Cl. .............................. 623/11; 623/1; 623/12; 128/898; 606/151
[58] Field of Search ................................. 623/1, 11, 12, 623/66; 606/151–153; 600/36; 128/898

[56] References Cited

U.S. PATENT DOCUMENTS

| | | |
|---|---|---|
| 3,783,454 | 1/1974 | Sausse et al. ........................ 623/12 |
| 3,818,511 | 6/1974 | Goldberg et al. .................. 623/12 X |
| 3,818,515 | 6/1974 | Neville ............................... 623/12 X |
| 3,833,940 | 9/1974 | Hartenbach ............................ 623/12 |
| 3,881,199 | 6/1975 | Treace . |
| 4,190,909 | 3/1980 | Ablaza ..................................... 623/1 |
| 4,225,979 | 10/1980 | Rey et al. . |
| 4,334,327 | 6/1982 | Lyman et al. ......................... 623/12 |
| 4,352,358 | 10/1982 | Angelchik . |
| 4,512,342 | 4/1985 | Zaneveld et al. .................. 623/12 X |
| 4,719,916 | 1/1988 | Ravo . |
| 4,721,095 | 1/1988 | Rey et al. ........................... 623/12 X |
| 4,732,152 | 3/1988 | Wallsten et al. . |
| 4,769,029 | 9/1988 | Patel ................................... 623/12 X |
| 4,822,333 | 4/1989 | Lavarenne .......................... 623/12 X |
| 4,854,316 | 8/1989 | Davis . |
| 4,878,906 | 11/1989 | Lindemann et al. .................... 623/1 |
| 4,905,693 | 3/1990 | Ravo ................................... 623/12 X |
| 4,990,131 | 2/1991 | Dardike et al. ....................... 623/1 X |
| 5,019,102 | 5/1991 | Hoene ...................................... 623/12 |
| 5,078,726 | 1/1992 | Kreamer ............................ 623/12 X |
| 5,147,370 | 9/1992 | McNamara et al. .................. 623/1 X |
| 5,192,289 | 3/1993 | Jessen ................................ 623/12 X |
| 5,246,456 | 9/1993 | Wilkinson ............................. 623/12 |
| 5,254,113 | 10/1993 | Wilk .................................. 623/12 X |
| 5,314,473 | 5/1994 | Godin ..................................... 623/12 |
| 5,316,023 | 5/1994 | Palmaz et al. .................... 623/12 X |

*Primary Examiner*—Paul B. Prebilic
*Attorney, Agent, or Firm*—Cushman, Darby & Cushman

[57] ABSTRACT

An anastomotic method for connecting a biological duct, such as the ureter, to a man-made device. The method involves connecting the duct to the prosthesis via an intermediate tissue so there is no direct connection between the ureter and the prosthesis. The method includes securing the resected duct to a remote living tissue, such as the peritoneum or omentum, and then securing that tissue to the prosthesis so that the duct drains into the prosthesis.

20 Claims, 1 Drawing Sheet

METHOD AND DEVICE FOR CONNECTING BIOLOGICAL DUCT TO A PROSTHESIS

BACKGROUND OF THE INVENTION

Implanted biological prostheses, for example a prosthetic ureter or a prosthetic urinary bladder, require methods and devices to make a connection with the biological structure (that connection is referred to hereinbelow as an anastomosis or as an anastomotic junction). The connection of tissue to a device poses many challenges because living tissue is easily damaged, can be induced to proliferate, or may join to itself and thereby close off the associated passage.

These challenges are demonstrated by canine implantation studies of anastomotic devices, which have exhibited several characteristic failure modes. The simplest of these anastomotic techniques involves the insertion of a tubular part into the biological tube, such as ureter. Between three and ten millimeters of the tip is placed inside the ureteral lumen and secured with permanent sutures. A seal is usually achieved by suturing the resected ureteral edge adjacent to a porous material to which the ureter will become affixed by ingrowth. For such methods, the tip of the inserted tube is tapered, rounded and smooth, since sharp edges or rough surfaces were expected to cause mechanical damage to the tissue. Such mechanical damage should be avoided because it probably initiates inflammation and drives some portions of the wound healing response, for example, the release of growth factors, with subsequent cell proliferation and activity. A similar design to that described above is illustrated in U.S. Pat. No. 4,225,979. Such insert-style anastomoses often fail because of papillary ureteral structures that block the entrance of the inserted tip.

Another prior, unsuccessful mode of anastomosis involves an end-to-end joining, where the perpendicularly resected biological ureter is abutted and directly sutured to a tubular structure of the urinary prosthesis. Canine ureters attached to such devices often develop a closed end, thus preventing transmission of urine to the device.

Attempts with an end-to-end anastomosis of the type used for vascular anastomoses have also failed. With that method matching spatulate end cuts are made on the parts to be attached. The spatulate spreads the sutures over a larger region, thus lessening the chances sutures will rub against each other; it also provides an easy way to join tubes with slightly different diameters. Anastomoses of this type have failed in both of the above-described ways.

In a fourth style of anastomosis, the ureter is inserted into the tubular structure and sutures to the tube are placed in the outer surface of the ureter a few millimeters from the resected end. The distal end of the ureter is allowed to dangle inside the tube. These anastomoses fail as a result of a blind end (cul-de-sac) of biological ureter forming at or just above the prosthetic device.

Because anastomotic failures of the type noted above prevent passage of biological fluids such as urine, the proximal ureter and kidney (in this example) develop hydronephrosis and ultimately the kidney for that ureter will fail.

At least a part of the difficulty of forming an anastomosis seems to be related to natural events, in particular, to peristaltic transport of fluids such as urine and to the epithelial lining, which has an inherent tendency to maintain its continuity. Peristaltic action is visible in the expansion of the diameter of the biologiccal tube such as ureter as a bolus of urine is pushed forward. Peristaltic waves occur regularly with their amplitude and frequency depending upon the amount of fluid such as urine that must be transported. In the case of ureter typically, there are a few waves per minute. As each wave passes, the lumen of the ureter changes from a collapsed, star-like cross-section, where the sides forming the arms of the star touch each other, to an open, polygonal shape, and then returns to the collapsed shape. The muscles in the ureteral wall force the polygonal shape to return to the collapsed shape and thus push the bolus of urine ahead. Because the ureteral wall muscles contract to push the bolus ahead, they force the lumenal surface against any object placed inside the ureter. The peristaltic process can also cause tugging motions on the anastomotic sutures that secure the biological ureter to the device.

Furthermore, the lumen of biological tubes such as ureter is lined with epithelium, a tissue that when cut or damaged, has an inherent propensity to repair itself and proliferate. In particular, when epithelial tissue is disrupted, the natural healing process acts to restore continuity of the epithelial surface. Since the ureter must be cut to connect it to the device that is to carry away urine, this natural process of restoring continuity of the epithelial surface is always initiated as a part of the surgical implantation. Cut epithelial surfaces that are held together for a short time can be expected to heal together and, thus, join.

Other implantable devices offer little guidance in designing anastomoses, such as ureteral ones. Vascular grafts of ureteral size are a current topic of research. In practice, most small vascular grafts are made by transplanting veins or arteries from another site. This method results in primarily a tissue-tissue junction, and hence avoids the problem of connecting tissue to exogenous or man-made materials. Percutaneous devices for the skin, another epithelial tissue, are also plagued by a host of problems, including downgrowth of epithelium which can result in expulsion of the device. One design strategy for percutaneous devices involves selecting materials for implantation and acute care protocols that result in a firm attachment of the collagenous subcutaneous tissue to the device. This strategy is being pursued with the expectation that the firmly attached underlying tissue will limit or frustrate the downgrowth of epithelium.

SUMMARY OF THE INVENTION

It is an object of the invention to provide an anastomotic method for biologic-synthetic junction, particularly for connecting the biological ureter to a man-made device, which overcomes the problems and failures experienced with the conventional anastomotic methods and devices noted above.

To achieve the foregoing and other objects, in accordance with the invention, an anastomotic method is provided for connecting the biological duct to a man-made device via an intermediate tissue so there is no direct connection between the ureter and the prosthesis.

Thus, in accordance with the invention, a method of connecting a biological duct to a prosthetic device is provided which includes providing a prosthesis having a first, open end and side walls depending therefrom; resecting a biological duct to which the prosthesis is to be attached to define a free end of the duct; selecting a segment of living tissue proximate to be not a part of the duct; securing the duct to a first portion of that tissue at a point spaced from the free end of the duct; securing a second portion of that tissue spaced from the first portion to the first end of the prosthesis so that the free end of the duct is disposed at least partially in the open end of the prosthesis, whereby the duct is indirectly coupled to the prosthesis and a passage defined through the duct is in flow communication with the prosthesis through the open end thereof.

Other objects, features, and characteristics of the present invention as well as the methods of operation and functions of the related elements of structure, and the combination of parts and economies of manufacture, will become more apparent upon consideration of the following description and the appended claims with reference to the accompanying drawings, all of which form a part of this specification, wherein like reference numerals designate corresponding parts in the various figures.

DETAILED DESCRIPTION OF THE PRESENTLY PREFERRED EXEMPLARY EMBODIMENTS

Figure 1:
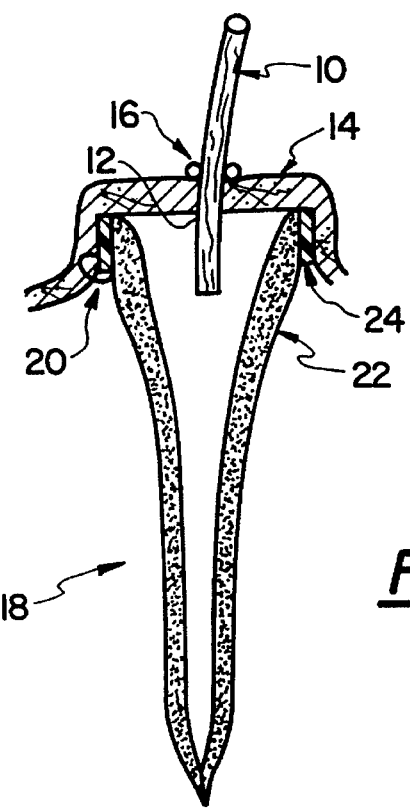
FIG. 1 is a cross-sectional view of a first embodiment of the method of the invention.
Figure 2:
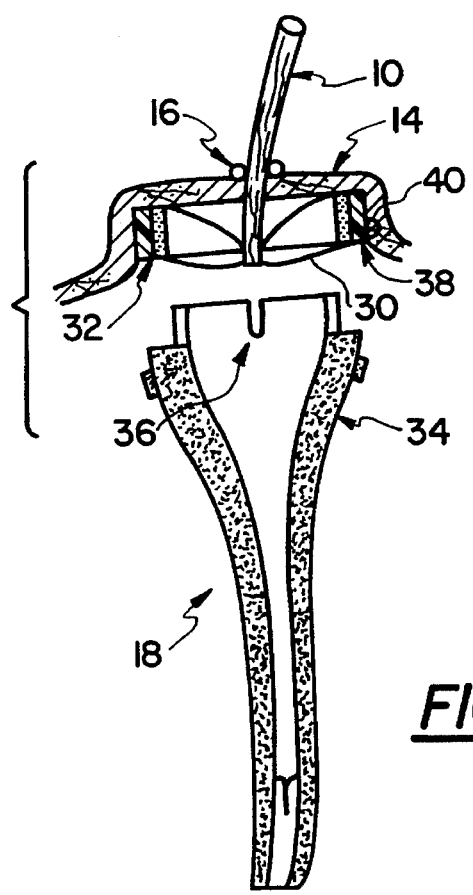
FIG. 2 is an exploded, cross-sectional view of a second embodiment of the method of the invention.

Two exemplary methods in accordance with the present invention are schematically illustrated in the cross-sectional views of FIGS. 1 and 2.

In accordance with the present invention, a biological duct, such as the biological ureter is indirectly coupled to a man-made device, such as a prosthetic bladder which has a urine inlet and a urine outlet, via an intermediate tissue herein referred to as a tissue bridge. In accordance with the method of the invention, there is no direct connection between the biological duct, e.g. ureter, and the prosthesis. As described more particularly below, the bridging tissue provides the resilient, accommodating interconnection necessary to allow the duct to freely expand and contract in response to the passage of fluid material therethrough thus avoiding irritation of the biological duct as a result of contact with the device inserted therein and/or damage or disruption from stress on suture sites which would otherwise encourage epithelial proliferation and duct closure. In accordance with the preferred embodiment of the invention, the tissue which forms a bridge from the ureter to the device is the omentum or peritoneum.

To perform the anastomosis, the duct 10 is resected at the desired location. The end of the duct e.g. the ureter, is brought through a small opening 12 in the bridging tissue 14 and ultimately sutured to it with biodegradable sutures 16. Several millimeters of ureter 10 are left extending below the tissue 14. The bridging tissue 14 is draped over the man-made device 18 and sutured to it with permanent sutures 20, for example those sold under the tradename PROLENE™.

The part of the device 18 into which the ureter 10 extends and onto which the bridging tissue 14 is draped is referred to herein as the acceptor portion 22. One region of the acceptor portion 22 is a surface 24 for attachment of the bridging tissue 14. As shown in FIG. 1, the site of tissue attachment is between the ureter 10 and the permanent sutures 20. The currently proposed method uses a microporous non-woven polyurethane fabric that supports tissue ingrowth. However, micropillared silicone elastomer, appropriate DACRON™ velour, or other material to which tissue intimately bonds, for example reactive glass-ceramics exhibiting soft tissue adhesions, may function equally well.

As noted above, the tissue bridge 14 affords special properties to the anastomotic junction. In a way it is the magic material that man cannot make. The tissue bridge is rapidly and naturally capable of attaching to both the ureter 10 and the microporous surface 24 on the acceptor portion 22. The type of tissue used for the bridge is a part of the abdominal defenses against foreign bodies and infections. Thus, its natural tendency is to engulf foreign material. After attachment, the tissue 14 provides a highly compliant, naturally repairing part of the anastomotic junction. Each peristaltic wave can stretch the tissue 14 without encountering significant resistance. The tissue bridge 14 is capable of virtually unlimited number of stretch/deformation cycles. Any minor damage will be naturally repaired as a part of the life process.

Furthermore, the epithelial tissue at the cut edges of the open end of the ureter is free to proliferate. Peristalsis repeatedly opens the lumen, thereby acting to prevent healing of the cut edges. Such action helps in meeting a key need, which is to keep the lumen at the end open so that as the epithelium proliferates it effectively forms and maintains a passage. The epithelium is free to grow back over the outside of the ureter 10, perhaps, even onto the bridging tissue 14. In that regard, it is expected that the epithelium will be stopped by the tight junction of bridging tissue 14 and device 18 at the microporous/attachment site on the acceptor portion 22. The opening of the acceptor portion 22, into which the ureter 10 extends and over which the bridging tissue 14 is spread should be sufficiently large to allow peristalsis of the ureter 10 without contact between the ureter 10 and device 18. It should also be large enough to allow for any swelling of the ureter that may occur due to the unavoidable trauma and handling associated with the surgical procedure.

In accordance with an alternate embodiment of the inventive process and device, biodegradable sutures 30 may be used to hold the resected end of ureter 10 open during the initial healing process. In the illustrated form of that embodiment, the surface to which the bridging tissue 14 is attached is a ring shaped piece 32. The ureter 10 is first passed through the bridging tissue 14 and then the ureter 10 is attached to the ring shaped piece 32 with the biodegradable sutures 30. The ring 32 is then slipped over the remaining, end portion 34 of the prosthetic device 18 and permanently attached thereto. As can be seen in FIG. 2, vertical slots 36 are defined in end portion 34 to accommodate sutures 30. Next, the bridging tissue 14 is attached to the ureter 10 with biodegradable sutures 16 and to the ingrowth promoting surface 38 of the ring 32 with sutures 40.

The materials for the bulk of the device should, of course, meet the unusual requirements for human implantation. Prototype devices have been made of medical grade silicone rubber elastomer, an implantable material from which thick-walled, yet flexible tubular structures are readily fabricated. Some provision must be made for securing the bridging tissue to the prosthetic device. As noted above, preferably a microporous surface 24, 38 is provided into which the tissue can grow which provides suture sites 20, 40 that are used to hold the tissue 10 in place during the ingrowth/healing phase. A microporous surface is preferred as such surfaces are associated with minimal amounts of fibrous encapsulation at the junction of bridging tissue and device. Since inflammation and tissue remodeling may affect nearby tissue, the choice of anchoring material must be made carefully.

To a limited extent, the inventive anastomotic design functions like a one-way valve because the ureteral lumen collapses at the end of each peristaltic wave. For a large part of the time, the end of the anastomosed ureter is a collapsed tube extending into a urine filled space. Any pressure rise at the end of the ureter also acts around the outside of the ureter. The collapsed lumen offers greater resistance to retrograde flow in the ureter and, equally important, the external pressure in the urine around the outside of the extended portion of the ureter acts to collapse it. The usable limit of the anastomosis and the one-way valve function is set by the strength of the bridging tissue and its attachment to the device and ureter.

In accordance with the most preferred form of the inventive prosthesis, an anti-reflux/backflow-limiting valve is further provided distal to the anastomotic junction. Such a valve limits the loads applied to the bridging tissue during the healing phases, allowing a strong connective tissue junction to develop between the bridging tissue and the device and probably also between the bridging tissue and, in the stated embodiment, the ureter. The need for such a anti-reflux/backflow-limiting valve increases as the area of the bridging tissue increases, since the force applied increases as the product of the back pressure with the effective area of the bridging tissue. The need for such a valve may be temporary and would be most important during the healing-in period, when the tissue-device connection is very tenuous. If only early healing is the issue, in lieu of a valve one could use a small balloon tip catheter placed in the prosthesis to take all discharged urine out of the body to avoid pressure applied to the tissue interface during the healing-in. In such a case, no valve will be the best design.

Exemplary anti-reflux/backflow limiting valves which may be provided in accordance with the invention are included in the embodiments of FIGS. 1 and 2. In the embodiment of FIG. 1, a duck bill type valve is formed at the end of the so-called prosthetic ureter. In the embodiment of FIG. 2, a so-called venous-style flap valve is formed in the tubular portion of the prosthesis. It should be noted that the valve types illustrated in FIGS. 1 and 2 are by way of example and not intended to be exhaustive. Furthermore, the embodiment in which each valve is shown is by way of example only and it should be understood that a duck-bill valve could be used with the embodiment of FIG. 2 and the flap valve used with the embodiment of FIG. 1.

The geometric nature of the anastomotic technique of the invention provides several additional unexpected advantages. For example, since the bridging tissue forms a diaphragm, it can result in a limited pumping capacity. Transient rises in abdominal pressure will induce the bridging tissue to bulge into the acceptor portion, assuming a relatively constant downstream pressure. As this occurs there is a concomitant action pushing urine out the exit of the device. Furthermore, the inventive design is significantly improved over simple intubating designs. In particular, the combination of a tissue bridge and the hanging, distensible ureter, in accordance with the invention, allows certain non-liquid materials to move from the ureter without interference. For example, small stones can be passed into the acceptor portion of the device. Furthermore, urinary mucus is unlikely to be caught in the prosthetic device as may occur with an intubating style of anastomosis.

While the invention has been described in connection with what is presently considered to be the most practical and preferred embodiment, it is to be understood that the invention is not to be limited to the disclosed embodiment, but on the contrary is intended to cover various modifications and equivalent arrangements included within the spirit and scope of the appended claims.

What is claimed:

1. A method of connecting a biological duct to a prosthetic device comprising:

providing a prosthesis having a first, open end and side walls depending therefrom;

resecting a biological duct to which said prosthesis is to be attached to define a free end of said duct;

selecting a segment of living tissue remote from said duct;

securing said duct to a first portion of said tissue at a point spaced from the free end of said duct;

securing a second portion of said tissue spaced from said first portion to said first end of said prosthesis so that said free end of said duct is disposed at least partially in said open end of said prosthesis, whereby said duct is indirectly coupled to said prosthesis and a passage defined through said duct is in flow communication with said prosthesis through said open end thereof.

2. A method as in claim 1, further comprising the steps of incising said living tissue to define an opening therethrough; and inserting said biological duct through said incision so that said duct extends through said segment of living tissue.

3. A method as in claim 2, wherein said duct is inserted through said living tissue so that said free end of said duct projects from a surface of said tissue.

4. A method as in claim 1, wherein said duct is a biological ureter.

5. A method as in claim 1, wherein said step of providing comprises providing a prosthesis which further comprises a second open end and a flow path defined between said first end and said second end.

6. A method as in claim 1, wherein said step of securing said duct to said tissue comprises suturing said duct to said tissue.

7. A method as in claim 6, wherein said step of suturing comprises suturing with biodegradable sutures.

8. A method as in claim 1, wherein said step of securing said tissue to said prosthesis comprises suturing said tissue to said prosthesis.

9. A method as in claim 8, wherein said prosthesis further comprises an area of tissue ingrowth media which allows said tissue to grow into said media.

10. A method as in claim 1, wherein said step of providing a prosthesis comprises providing a prosthesis including a ring element and a main body portion, said ring element being secured to said main body portion to define said first open end, said tissue being secured to said ring element.

11. A method as in claim 10, wherein said ring element is secured to an outer surface of said main body portion.

12. A method as in claim 10, further comprising the step of guiding suture material into and through said duct adjacent said free end and through a surface of said prosthesis thereby to maintain said free end of said duct in an open configuration during initial healing, said suture material being biodegradable whereby said sutures gradually degrade and become ineffective.

13. A method as in claim 1, further comprising the step of guiding suture material into and through said duct adjacent said free end and through a surface of said prosthesis thereby to maintain said free end of said duct in an open configuration during initial healing, said suture material being biodegradable whereby said sutures gradually degrade and become ineffective.

14. A method as in claim 12, wherein said step of guiding suture material includes guiding suture material through said ring element.

15. A method as in claim 14, wherein said step of providing a prosthesis comprises providing a main body portion having a plurality of vertical slots, each for receiving a said suture when said ring is attached to said main body portion.

16. A method as in claim 1, wherein said first end of said prosthetic device is substantially circular and said prosthetic device is mounted in concentric, surrounding relation to said duct and secured to said tissue whereby said first end of said prosthetic device is disposed in spaced relation to said free end of said duct.

17. A method as in claim 1, wherein said living tissue is the omentum.

18. A method as in claim 1, wherein said living tissue is the peritoneum.

19. A method as in claim 1, wherein said step of providing comprises providing a prosthesis which further comprises a generally tubular second end portion which is collapsed so as to define a one way valve.

20. A method as in claim 1, wherein said step of providing comprises providing a prosthesis which further comprises a generally tubular second end portion having a one-way valve provided therewithin for controlling the direction of flow therethrough.

* * * * *